US00PP34914P2

(12) United States Plant Patent
Hardigan et al.

(10) Patent No.: US PP34,914 P2
(45) Date of Patent: Jan. 17, 2023

(54) BLACKBERRY PLANT NAMED 'THUNDERHEAD'

(50) Latin Name: ***Rubus* subg. *Rubus* Watson**
Varietal Denomination: Thunderhead

(71) Applicant: The United States of America, as represented by the Secretary of Agriculture, Washington, DC (US)

(72) Inventors: Michael A. Hardigan, Corvallis, OR (US); Chad E. Finn, Corvallis, OR (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 17/697,907

(22) Filed: Mar. 17, 2022

(51) Int. Cl.
*A01H 5/08* (2018.01)
*A01H 6/74* (2018.01)

(52) U.S. Cl.
USPC ..... Plt./203

(58) Field of Classification Search
USPC ..... Plt./203
CPC ... A01H 5/08; A01H 5/00; A01H 6/74; A01H 6/7499
See application file for complete search history.

(56) References Cited

U.S. PATENT DOCUMENTS

PP22,449 P3 * 1/2012 Clark ..... A01H 5/08 Plt./203
PP26,990 P3 * 8/2016 Clark ..... A01H 5/08 Plt./203

OTHER PUBLICATIONS

Sanford et al. Titan' Red Raspberry New York's Food and Life Sciences Bulletin, No. 111, 1985, pp. 1-3. (Year: 1985).*
Southeast AgNet Radio Network 2020 retrieved on Apr. 12, 2022 at Internet at https://southeastagnet.com/2020/10/21/new-blackberries-eclipse-galaxy-and-twilight/, 4 pp. (Year: 2020).*

* cited by examiner

*Primary Examiner* — June Hwu
(74) *Attorney, Agent, or Firm* — John Fado; Ariel Atkinson

(57) ABSTRACT

A new and distinct blackberry cultivar that originated from seed produced from a cross between the thorny primocane-fruiting maternal blackberry plant ORUS 4355-2 and the thornless primocane-fruiting paternal blackberry plant 'Prime-Ark® Freedom'. 'Thunderhead' is the first primocane-fruiting blackberry variety released by the USDA-ARS breeding program in Oregon. This new blackberry cultivar can be distinguished by its exceptionally high plant vigor and yields of medium sized berries with high gloss, firmness, excellent flavor and fruit quality, and relatively small seed size. The berries are well suited for fresh eating, with good sweetness and gloss when picked firm, and low bitter notes. The new and distinct blackberry variety contains a genetic background derived from eastern U.S. germplasm and is expected to grow and is expected to perform well in most areas where primocane-fruiting blackberries are currently grown.

6 Drawing Sheets

Latin name of the genus and species of the plant claimed: 'THUNDERHEAD' is a blackberry plant that is *Rubus* subg. *Rubus* Watson.

Variety denomination: The new blackberry plant claimed is of the variety denominated 'Thunderhead' *Rubus* subg. *Rubus* Watson.

BACKGROUND OF THE NEW PLANT

The present invention relates to a new and distinct blackberry cultivar designated 'Thunderhead' and botanically known as *Rubus* subg. *Rubus* Watson. This new primocane-fruiting blackberry cultivar was discovered in Corvallis, Oreg. in August 2016, and is the result of a 2014 cross between the maternal blackberry plant ORUS 4355-2 (unpatented) and the paternal blackberry plant 'APF-153T' (U.S. Plant Pat. No. 26,990), known as the trade name 'Prime-Ark® Freedom'. ORUS 4355-2 was a thorny primocane-fruiting selection from a cross of the thorny primocane-fruiting blackberry NC 538 (unpatented) and thorny primocane-fruiting blackberry 'APF-45' (U.S. Plant Pat. No. 22,449), known as the trade name Prime-Ark® 45. 'Prime-Ark® Freedom' was a thornless primocane-fruiting selection from a cross of the blackberry plant AR 2301 (unpatented) and the thornless primocane-fruiting blackberry plant APF 49T (unpatented). The original seedling of the new cultivar was asexually propagated in Benton County, Oreg. The new cultivar was established in vitro from a cane cutting and microcuttings have been taken and rooted from this sort of culture. The present invention has been found to be stable and reproduce true to type through successive asexual propagations.

SUMMARY OF THE NEW PLANT

The following are the most outstanding and distinguishing characteristics of this new cultivar when grown under normal horticultural practices in Oregon. The new cultivar possesses an erect, primocane-fruiting habit. The cultivar compensates for a lack of complete genetic thornlessness with exceptionally high plant vigor and exceptionally high yields of fruit for a primocane-fruiting type with excellent flavor and quality for the fresh market that is at least on par with than current primocane-fruiting varieties. In Oregon trials, the new cultivar established more quickly in the field than other primocane-fruiting varieties and was able to produce a $2^{nd}$ year baby-crop that yielded higher than full harvest yields in many of the older, more established blackberry trial plots. The new cultivar is mid-season for a primocane-fruiting blackberry grown in Oregon, ripening at a similar time to 'Prime-Ark® 45' but with 1.4-to-1.9-fold higher yields over the 2019-2021 growing seasons. In addition to its exceptional plant vigor and yield potential, the new cultivar produces berries with excellent fruit quality that is competitive with current fresh market cultivars. The berries are sweet even when picked firm and show a good combination of firmness and skin toughness without being chewy. Compared to older fresh market blackberries the new cultivar contains fewer bitter notes and smaller, less noticeable seeds. The new cultivar ranked highest for flavor among all primocane-fruiting blackberry samples in the most recent Oregon State University food science survey of stakeholders conducted in 2019. The post-harvest shelf life appears to be on par with other fresh market primocane-fruiting varieties, with berries able to sit for 23 d in cold storage without substantial deterioration or mold growth. No significant disease resistance or susceptibility has been observed in 'Thunderhead'.

BRIEF DESCRIPTION OF THE PHOTOGRAPHS

This new blackberry plant is illustrated by the accompanying photographs that show the plants, ripening fruit morphology, and harvested fruit; the colors shown are as true as can be reasonably obtained by conventional photographic procedures.

DETAILED DESCRIPTION OF THE NEW CULTIVAR

Figure 1:
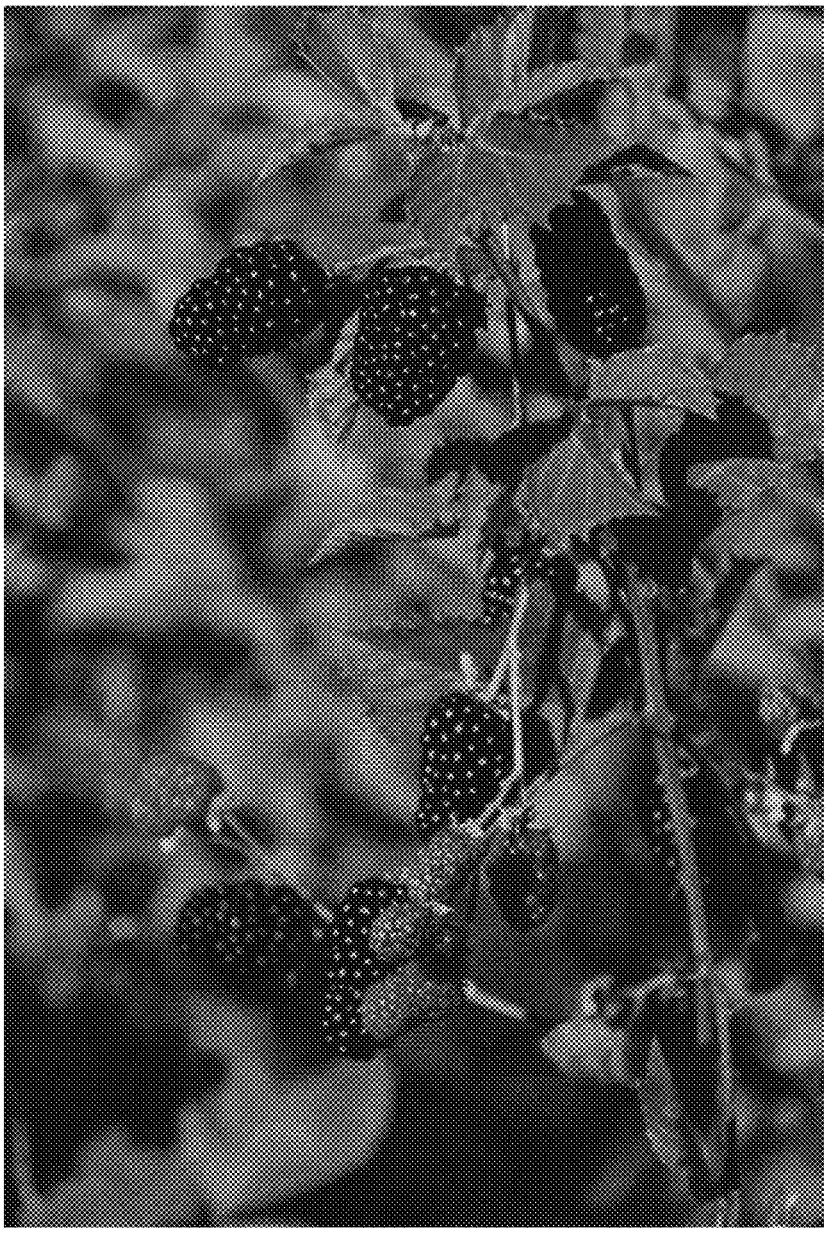
FIG. 1 shows an example of a fruiting cluster with ripe 'Thunderhead' fruit.
Figure 2:
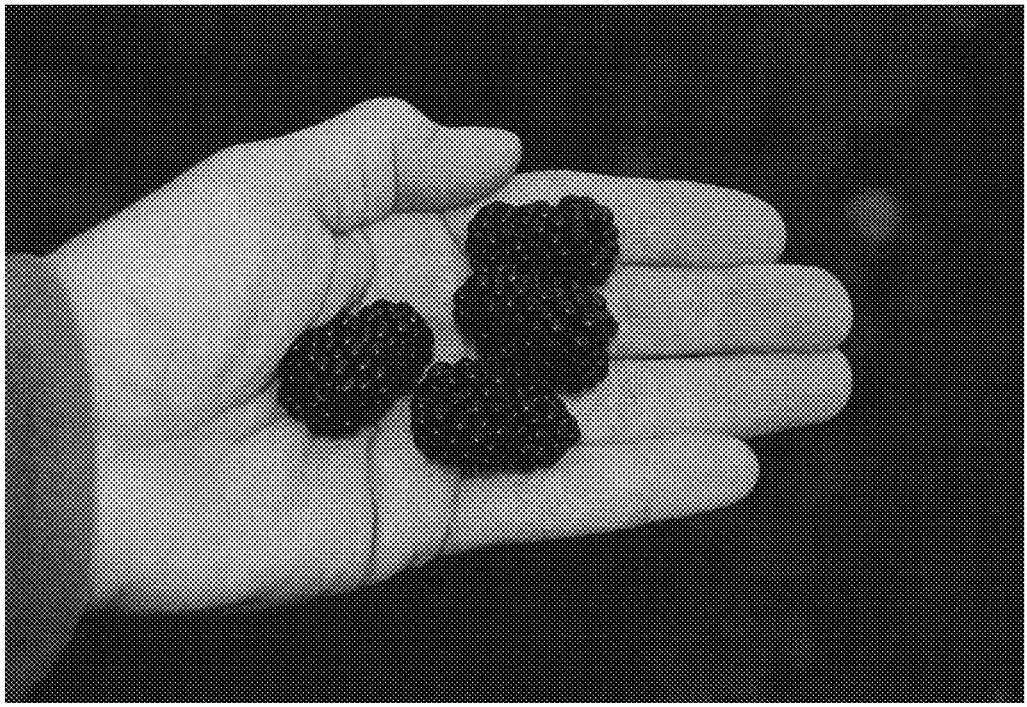
FIG. 2 shows a close-up example of the size and shape of 'Thunderhead' fruit.
Figure 3:
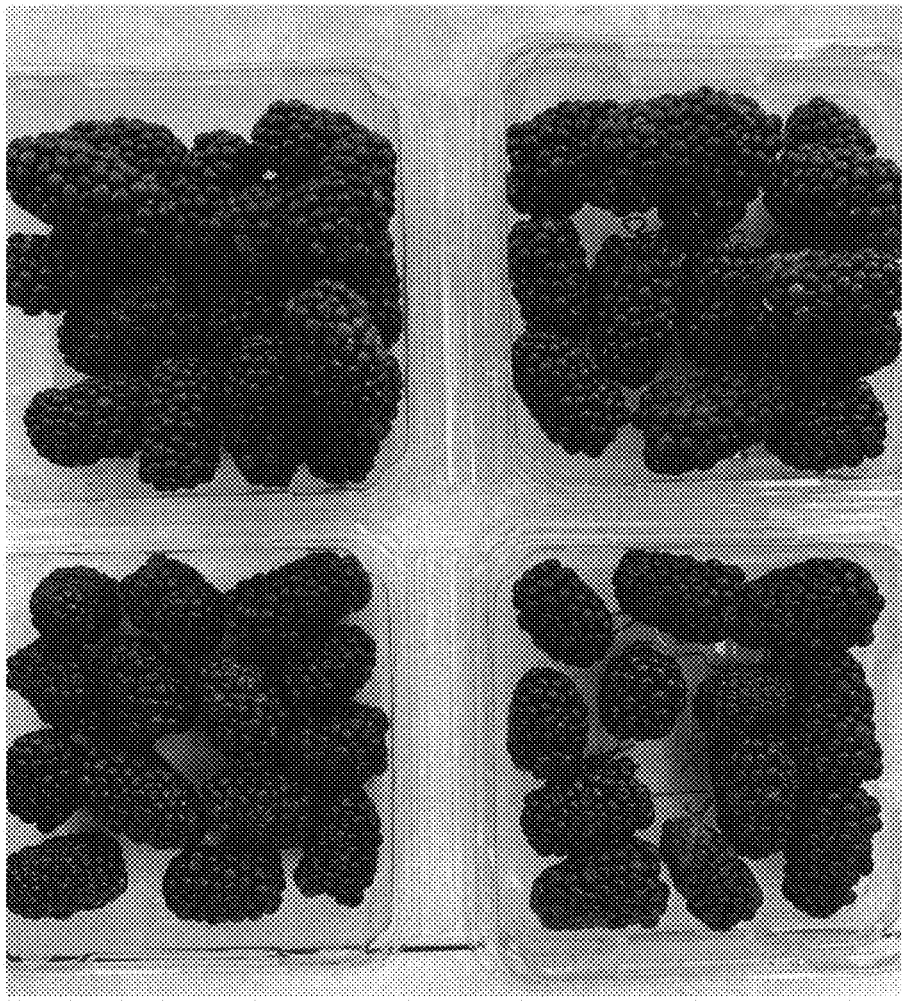
FIG. 3 shows a clamshell of 'Thunderhead' fruit (left) and 'Prime-Ark 45' fruit (right) after 23 days of refrigerated storage at ~4° C.
Figure 4:
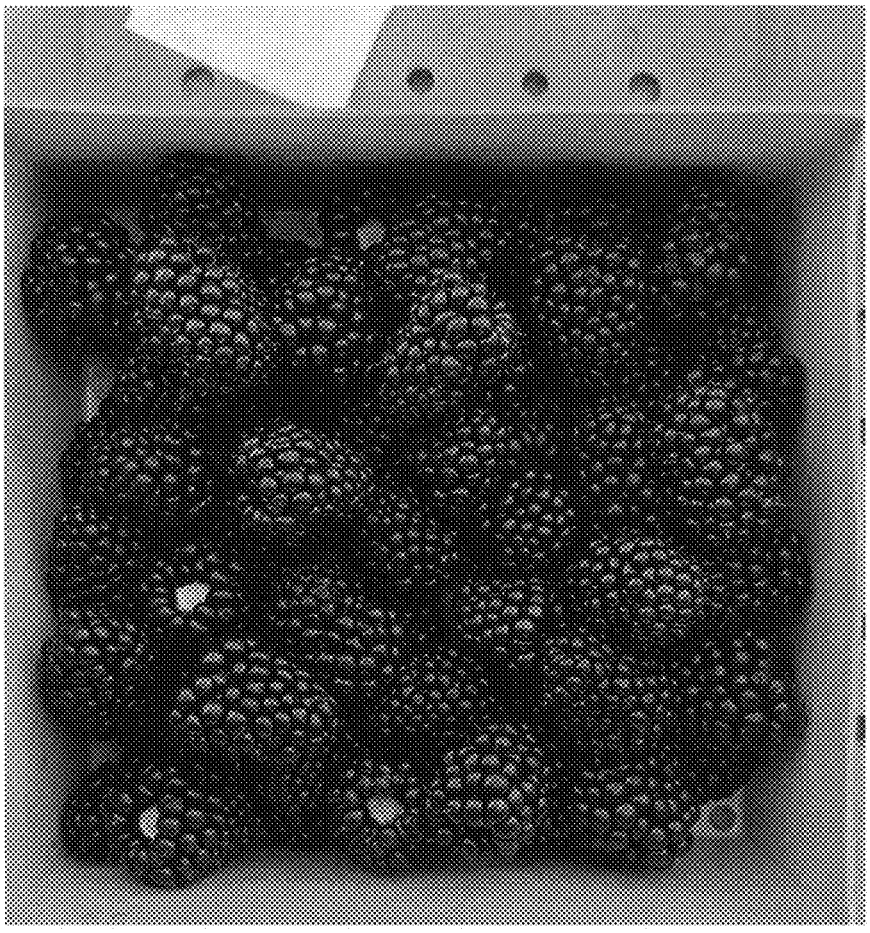
FIG. 4 shows a flat of freshly harvested 'Thunderhead' fruit.
Figure 5:
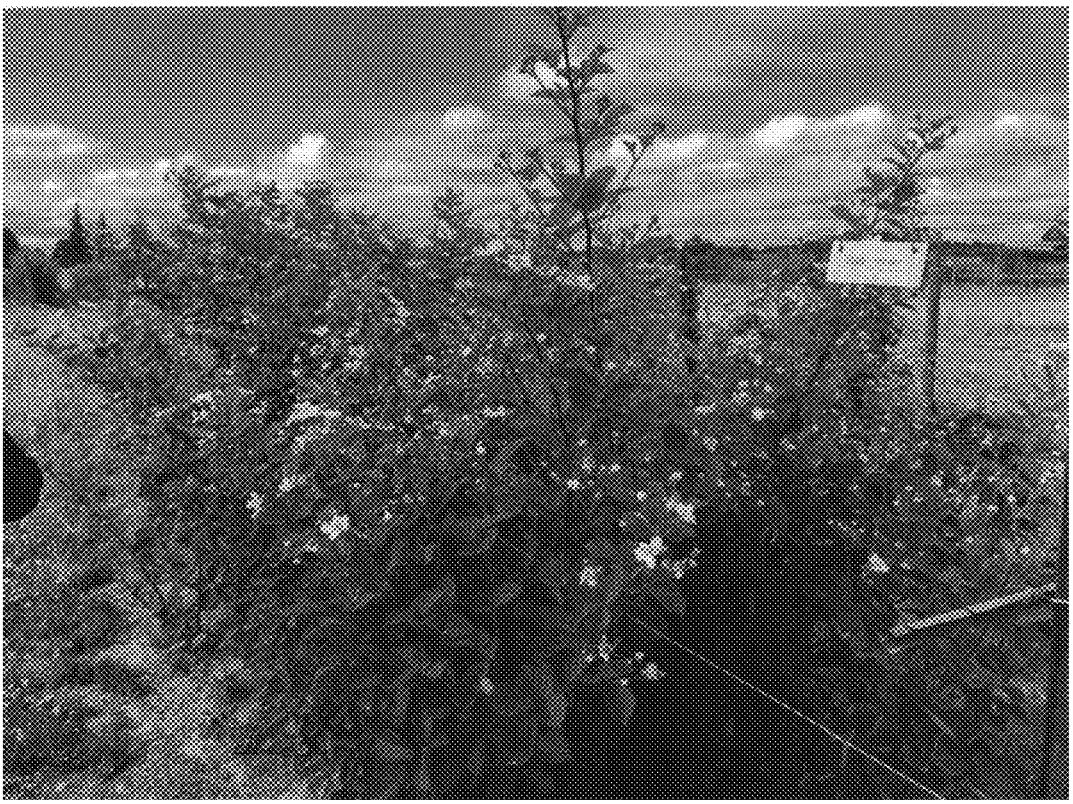
FIG. 5 shows a 2 year old plot of entire 'Thunderhead' plants during flowering in late July.
Figure 6:
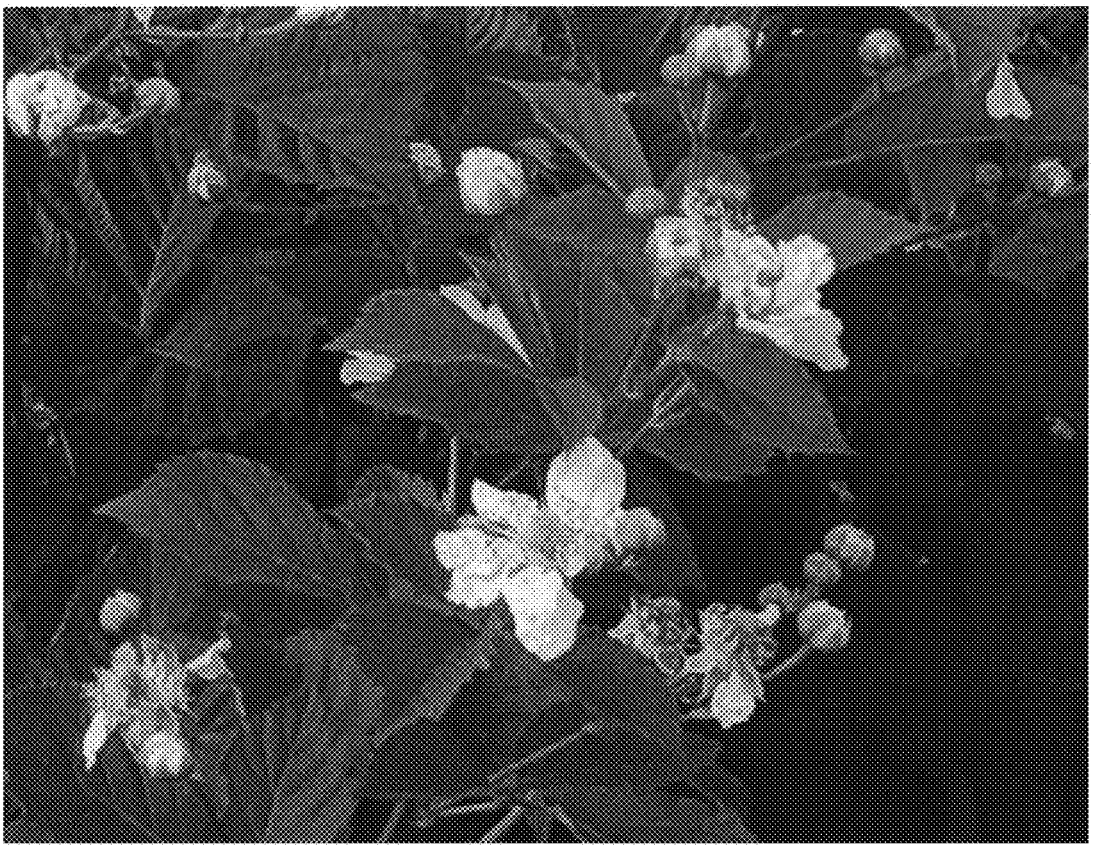
FIG. 6 shows the morphology of 'Thunderhead' flowers.

The following description of 'Thunderhead' is based on observations taken from 2016 to 2021 growing seasons in trials in Corvallis and Aurora, Oreg. This description is in accordance with UPOV terminology. Color designations, color descriptions and other phenotypical descriptions may deviate from the stated values and descriptions depending upon variation in environmental, seasonal, climatic, and cultural conditions. 'Thunderhead' has not been observed under all possible environmental conditions. Color terminology follows The Royal Horticultural Society Colour Chart. London (R.H.S.) ($5^{th}$ edition, 2007).

Table 1 shows plant characteristics of the new cultivar. Characteristics include plant vigor, growth habit, date of bud-break, presence of spines further than 0.6 m from the soil surface, presence of spines less than 0.6 m from the soil surface, weight of primary fruit, uniformity of berry shape, fruit firmness, fruit flavor, fruit soluble solids (%; in Brix), fruit pH, fruit titratable acidity (% as citric acid), and yield (actual kg•plt−1). Fruit measurements are from 2020 trial data collected from OSU-NWREC (Aurora, Oreg.).

TABLE 1

| Characteristic | Thunderhead | Prime-Ark ® 45 |
|---|---|---|
| Plant vigor | Very High | High |
| Growth habit | Erect/Primocane-fruiting | Erect/Primocane-fruiting |
| Date of budbreak | Week 3, March (2021) | Week 2, March (2021) |
| Presence of spines further than 0.6 m from the soil surface | Low-Moderate | Moderate |
| Presence of spines less than 0.6 m from the soil surface | Moderate | Moderate |
| Weight of primary fruit | 8.2-10.4 g | 11.0 g |
| Uniformity of berry shape | Good | Good |
| Fruit firmness | Very good | Very good |
| Fruit flavor | Very good | Good |
| Fruit gloss | Very good | Good |
| Texture of fruit when chewed | Very good | Moderate |
| Drupelet skin resistance to abrasion | Very good | Good |
| Fruit soluble solids (%; in Brix) | 15.08 | 15.87 |
| Fruit pH | 3.52 | 3.40 |
| Fruit titratable acidity (% as citric acid) | 11.00 | 1.33 |
| Yield (actual kg · plt-1) | 8.32 | 5.25 |

Table 2 shows floricane and mature primocane characteristics of the new cultivar. Characteristics include diameter at base, diameter at midpoint, diameter at terminus, internode length at base, internode length at midpoint, internode length at terminus, presence of spines further than 0.6 m from the soil surface, presence of spines less than 0.6 m from the soil surface, floricane color at base, floricane color at midpoint, floricane color at terminus, floricane lateral length, floricane lateral strength, primocane color at base, primocane color at midpoint, primocane color at terminus, and floricane length (range).

TABLE 2

| Characteristic | Thunderhead |
|---|---|
| Diameter at base | 1.65 cm |
| Diameter at midpoint | 1.24 cm |
| Diameter at terminus | 0.31 cm |
| Internode length at base | 5.85 cm |
| Internode length at midpoint | 5.81 cm |
| Internode length at terminus | 2.37 cm |
| Presence of spines further than 0.6 m from the soil surface | Low-Moderate |
| Presence of spines less than 0.6 m from the soil surface | Moderate |
| Attitude of spine in relation to the cane | Outwards |

TABLE 2-continued

| Characteristic | Thunderhead |
|---|---|
| Floricane color at base | NA (primocane type) |
| Floricane color at midpoint | NA (primocane type) |
| Floricane color at terminus | NA (primocane type) |
| Floricane lateral length | NA (primocane type) |
| Floricane lateral strength | NA (primocane type) |
| Primocane color at base | RHS 187B |
| Primocane color at midpoint | RHS 145A |
| Primocane color at terminus | RHA 183A |
| Floricane length (range) | NA (primocane type) |

Table 3 shows primocane foliage characteristics of the new cultivar. Primocane characteristics include mature compound leaf width, mature compound leaf length, number of leaflets per primocane compound leaf, mature leaflet shape, mature leaflet apex, mature leaflet base, mature terminal leaflet width, mature terminal leaflet length, mature first lateral leaflet width, mature first lateral leaflet length, leaflet margin, leaflet serration teeth length, leaflet serration teeth width at base, spine presence on leaves, pubescence on primocane leaflet: upper surface, pubescence on primocane leaflet: undersurface, primocane leaf color abaxial, primocane leaf color adaxial, petiole length, petiole color: upper surface, petiole color: undersurface, petiolule length: terminal leaflet, petiolule length: first distal leaflet, petiolule color: abaxial, petiolule color: adaxial, stipule length, and stipule width.

TABLE 3

| Characteristic | Thunderhead |
|---|---|
| Mature compound leaf width | 15.35 cm |
| Mature compound leaf length | 16.12 cm |
| Number of leaflets per primocane compound leaf | Usually 3-5 |
| Mature leaflet shape | Ovate to round |
| Mature leaflet apex | Acuminate abruptly |
| Mature leaflet base | Cordate |
| Mature terminal leaflet width | 5.97 cm |
| Mature terminal leaflet length | 7.58 cm |
| Mature first lateral leaflet width | 5.57 cm |
| Mature first lateral leaflet length | 7.07 cm |
| Leaflet margin | Serrate |
| Leaflet serration teeth length | 0.80 cm |
| Leaflet serration teeth width at base | 0.63 cm |
| Spine presence on leaves | Absent or few |
| Pubescence on primocane leaflet: upper surface | Light/sparse |
| Pubescence on primocane leaflet: undersurface | Light/even |
| Primocane leaf color abaxial | RHS 146B |
| Primocane leaf color adaxial | RHA 146A |
| Petiole length | 7.95 cm |
| Petiole color: upper surface | RHS 149A |
| Petiole color: undersurface | RHS 185A |
| Petiolule length: terminal leaflet | 26.30 cm |
| Petiolule length: first distal leaflet | 19.76 cm |
| Petiolule color: abaxial | RHS 60C |
| Petiolule color: adaxial | RHS 150B |
| Stipule length | 1.48 cm |
| Stipule width | 0.68 cm |

Table 4 shows flower and flowering characteristics of the new cultivar. Flower and flowering characteristics include date 1st bloom, date full bloom, date last bloom, petal color, number flowers per cluster, number of petals per flower, flower diameter, petal length, petal width, and number of sepals per flower.

TABLE 4

| Characteristic | Thunderhead |
|---|---|
| Date 1st bloom | 10-July |
| Date full bloom | 24-July |
| Date last bloom | 24-August |
| Petal color | RHS 155D |
| Number flowers per cluster | 18.00 |
| Number of petals per flower | 7-10 |
| Flower diameter | 3.68 cm |
| Petal length | 1.68 cm |
| Petal width | 1.24 cm |
| Number of sepals per flower | 5-6 |
| Peduncle length (cm) | 4.68 |
| Rachis length (cm) | 11.47 |
| Peduncle color | RHS 60B |
| Cyme type | Elongate simple cyme |

Table 5 shows fruit and fruiting characteristics of the new cultivar. Fruit and fruiting characteristics include date 5% of fruit were ripe, date 50% of fruit were ripe, date 95% of fruit were ripe, weight of primary fruit, weight of secondary fruit, weight of tertiary fruit, diameter of primary fruit at equator, diameter of 2° fruit at equator, diameter of 3° fruit at equator, diameter of 1° fruit at poles: tip, diameter of 1° fruit at poles: base, diameter of 2° fruit at poles: tip, diameter of 2° fruit at poles: base, diameter of 3° fruit at poles: tip, diameter of 3° fruit at poles: base, berry length primary fruit, berry length 2° fruit, berry length 3° fruit, ratio of primary fruit length to width, shape description, uniformity of berry shape, color when full ripe, number of drupelets per fruit, individual seed weight, glossiness, firmness, flavor, texture of fruit when chewed, drupelet skin resistance to abrasion, ease of separation of fruit from pedicel, machine harvestability, resistance to heat damage of fruit, berries per inflorescence—mean, berries per inflorescence range, soluble solids (%; in Brix), pH, titratable acidity (% as citric acid), and yield (actual kg•plt−1). Fruit chemistry data is from 2020 field season at OSU-NWREC.

TABLE 5

| Characteristic | Thunderhead |
|---|---|
| Date 5% of fruit were ripe | 14-August |
| Date 50% of fruit were ripe | 10-September |
| Date 95% of fruit were ripe | Fruits until first Fall frost |
| Fruiting lateral length | 20-40 cm |
| Weight of primary fruit | 10.40 g |
| Weight of secondary fruit | 7.27 g |
| Weight of tertiary fruit | 5.95 g |
| Diameter of primary fruit at equator | 2.28 cm |
| Diameter of 2° fruit at equator | 2.05 cm |
| Diameter of 3° fruit at equator | 1.98 cm |
| Diameter of 1° fruit at poles: tip | 1.51 cm |
| Diameter of 1° fruit at poles: base | 2.16 cm |
| Diameter of 2° fruit at poles: tip | 1.30 cm |
| Diameter of 2° fruit at poles: base | 1.87 cm |
| Diameter of 3° fruit at poles: tip | 1.19 cm |
| Diameter of 3° fruit at poles: base | 1.95 cm |
| Druplets size | Small to medium |
| Berry length primary fruit | 3.48 cm |
| Berry length 2° fruit | 2.94 cm |
| Berry length 3° fruit | 2.71 cm |
| Ratio of primary fruit length to width | 1.54 |
| Shape description | Blocky to conical |
| Uniformity of berry shape | Medium |
| Color when full ripe | RHS 203B |
| Number of drupelets per fruit | 157 |
| Individual seed weight | 2.61 mg |
| Glossiness | Medium to high |
| Firmness | Very firm |

TABLE 5-continued

| Characteristic | Thunderhead |
|---|---|
| Flavor | Very good |
| Texture of fruit when chewed | Very good |
| Drupelet skin resistance to abrasion | Excellent |
| Ease of separation of fruit from pedicel | Very easy |
| Machine harvestability | NA (only picked fresh) |
| Resistance to heat damage of fruit | Very good |
| Berries per inflorescence - mean | 12 |
| Berries per inflorescence range | 8-15 |
| Soluble solids (%; in Brix) | 15.08 |
| pH | 3.52 |
| Titratable acidity (% as citric acid) | 11.00 |
| Yield (actual kg · plt-1) | 8.32 |

COMPARISON WITH PARENTAL AND COMMERCIAL VARIETIES

'Thunderhead' differs from the female parent blackberry plant ORUS 4355-2 in that it has a more vigorous plant with significantly greater yields. The fruit are slightly smaller than ORUS 4355-2, but it produces larger numbers with a higher number of fruits per lateral. The 'Thunderhead' fruit quality is improved with robust firmness and flavor and appears less susceptible to mold and red berry mite (RBM).

'Thunderhead' differs from the male parent blackberry plant 'Prime-Ark® Freedom' in that it lacks complete genetic thornlessness, shows higher yields and plant vigor, and produces larger numbers of smaller-sized berries with a more consistent/uniform shape and a smaller, more uniform drupelet size. The 'Thunderhead' flavor is less astringent when grown in Oregon.

'Thunderhead' differs from the primocane-fruiting blackberry variety 'Prime-Ark® 45' in that it has shown higher fruit yields within a similar ripening season/window when grown in Aurora, Oreg. The 'Thunderhead' fruit are slightly smaller, with smaller individual drupelet size and somewhat higher drupelet uniformity. The fruit were similarly glossy and sweet to 'Prime-Ark® 45', with a similar shelf life and post-harvest appearance after 23 days in refrigerated storage in plastic clam shell packaging at 4° C. The 'Thunderhead' fruit contain slightly lower bitter notes than 'Prime-Ark® 45', and smaller less noticeable seeds.

We claim:

1. A new and distinct cultivar of blackberry plant named 'Thunderhead', substantially as illustrated and described, characterized by its plant vigor, and exceptional yields of medium sized berries with excellent fresh eating quality, firmness, and flavor, with small seed size.

* * * * *